US007914520B2

(12) United States Patent
Kennedy, II

(10) Patent No.: US 7,914,520 B2
(45) Date of Patent: Mar. 29, 2011

(54) MEDICAL CATHETERS OF MODULAR CONSTRUCTION

(75) Inventor: Kenneth C. Kennedy, II, Clemmons, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 880 days.

(21) Appl. No.: 11/637,433

(22) Filed: Dec. 12, 2006

(65) Prior Publication Data

US 2007/0142820 A1    Jun. 21, 2007

Related U.S. Application Data

(60) Provisional application No. 60/752,179, filed on Dec. 19, 2005.

(51) Int. Cl.
*A61M 25/16* (2006.01)
(52) U.S. Cl. ...................................................... 604/534
(58) Field of Classification Search ................. 604/523, 604/524, 525, 526, 527, 528, 534, 535, 264; 600/101, 121, 139, 140–143
See application file for complete search history.

(56) References Cited

U.S. PATENT DOCUMENTS

| 5,824,031 | A | * | 10/1998 | Cookston et al. | ............ | 607/122 |
| 6,249,708 | B1 | * | 6/2001 | Nelson et al. | ................. | 607/122 |
| 6,942,648 | B2 | | 9/2005 | Schaible et al. | ............... | 604/264 |
| 7,077,823 | B2 | * | 7/2006 | McDaniel | .................. | 604/95.01 |
| 2004/0097965 | A1 | * | 5/2004 | Gardeski et al. | .............. | 606/129 |

FOREIGN PATENT DOCUMENTS

| EP | 1 321 163 | 6/2003 |
| WO | WO 98/29055 | 7/1998 |

OTHER PUBLICATIONS

International Search Report and Opinion for PCT/US2006/047482.
Examiner's Report dated Mar. 12, 2010 for Canadian Application No. 2,633,664 (3 pgs).

* cited by examiner

*Primary Examiner* — Manuel A Mendez
(74) *Attorney, Agent, or Firm* — Brinks Hofer Gilson & Lione

(57) ABSTRACT

The present invention is directed to medical catheters that may be modularly constructed to facilitate manufacture and provide properties that may be difficult to achieve with a catheter formed from a single extrusion or multiple materials that are fused together. The catheter may be constructed of one or more core elements that may be partially or fully surrounded by a jacket member in a variety of configurations. The core elements may comprise different properties with respect to the jacket member or one another, thereby permitting increased manufacturing flexibility. The modular catheter designs of the present invention further provide for a variety of lumen configurations, as well as providing for catheters that can change their shape by moving the core elements with respect to the jacket member or one another.

13 Claims, 7 Drawing Sheets

MEDICAL CATHETERS OF MODULAR CONSTRUCTION

PRIORITY CLAIM

This invention claims the benefit of priority of U.S. Provisional Application Ser. No. 60/752,179, entitled "Medical Catheters of Modular Construction," filed Dec. 19, 2005, the disclosure of which is hereby incorporated by reference in its entirety.

BACKGROUND INFORMATION

This invention relates to medical catheters, and more particularly, to catheters formed from one or more modular elements.

Medical catheters serve various functions. The catheters may be employed in a number of procedures ranging from interventional stroke treatment, angioplasty procedures, aneurysm treatment procedures, and many other operations. Catheters may be used in conjunction with one or more wire guides that facilitate introduction of the catheter to a desired site. The catheters may infuse or aspirate fluid, deliver instruments, perform imaging operations, and/or may be used for other purposes during a procedure.

Medical catheters may be adapted for insertion into numerous bodily regions, such as vessels or ducts. Such catheters may be relatively rigid or flexible, and may be substantially uniform or vary along their lengths, depending on the needs of the procedure, the vessels or ducts involved, and other variables associated with an operation.

Many polymeric catheters currently are manufactured from a single extrusion having one or more lumens. For example, melted polymeric material may be extruded using a die, then passed into a quench bath to form the catheter structure. A multiple layer catheter may be co-extruded, or a second layer may be extruded over an existing polymeric tube. Thermal processing techniques may be employed to bond two materials together, or alternatively, adhesives may be employed.

A typical catheter extrusion process may have various limitations. For example, it may be difficult to vary the profile, properties or characteristics along the longitudinal axis of the catheter using a single extrusion. Also, if thermal techniques are employed to secure two catheter materials together, limitations may arise when dealing with processing temperatures used to form an adhesive bond. If an adhesive is used to affix multiple catheter elements, further steps associated with the adhesion process are required.

Moreover, the addition of features to a catheter of single extrusion may be difficult or require complex secondary operations. For example, the addition of side ports, tips and other features to an extruded catheter may require additional components or manufacturing steps.

Therefore, there is a need for a catheter that may be modularly constructed to facilitate manufacture and provide properties that may be difficult to achieve with a catheter formed from a single extrusion or multiple elements that are bonded together.

SUMMARY

The present invention provides various medical catheters that may be modularly constructed to facilitate manufacture and provide properties that may be difficult to achieve with a catheter formed from a single extrusion. The medical catheters generally comprise one or more core elements that may be partially or completely enclosed by a jacket member.

In a first embodiment of the invention, a catheter comprises a core element having proximal and distal regions, an exterior surface and a longitudinal axis. At least one channel is formed in the exterior surface of the core element. The channel extends along at least a portion of the longitudinal axis of the catheter and is at least partially surrounded by a jacket member, thereby forming at least one side lumen in the catheter. Advantageously, the side lumen may be relatively small and may be disposed near an exterior surface of the catheter. Such a lumen may be difficult to achieve using previously-known manufacturing techniques. Further, the channel may not be covered by the jacket member at selected longitudinal locations to provide at least one access port into the side lumen of the catheter. The access port may be used, for example, in a rapid-exchange catheter configuration.

In another embodiment of the present invention, a modular catheter is provided comprising a first core element having proximal and distal regions and a longitudinal axis, a second core element having proximal and distal regions and a longitudinal axis, and a jacket member disposed at least partially around the first core element and the second core element. The catheter is adapted for insertion into a selected body cavity. In one embodiment, the first core element may be longitudinally movable with respect to the second core element. Further, the first core element and/or second core elements may comprise an indentation formed in a lateral surface thereof, wherein the indentations may house a third core element, or alternatively, may form a void region suitable for use as a catheter lumen.

In a further alternative embodiment, the first core element may comprise a longitudinal bore formed therein, and the second core element may comprise a substantially circular shape that is adapted for insertion into the longitudinal bore. The second core element may extend distal to the first core element, thereby allowing the catheter to comprise a distal region of reduced cross-section relative to a proximal region of the catheter.

Alternatively, the first core element may be disposed proximal to the second core element, such that a distal region of the first core element abuts a proximal region of the second core element. In this embodiment, the first core element and the second core element may be formed of materials having different properties to enable the catheter to achieve differing flexibilities along a longitudinal axis.

In still a further alternative embodiment, a catheter having proximal and distal regions comprises a core element having first and second ends, and further having constrained and expanded states. A jacket member is configured to encircle the core element in the constrained state, wherein the core element is held in the constrained state by the jacket member such that the first and second ends form a substantially circular shape that conforms to an interior surface of the jacket member. The core element may be provided with a working lumen formed when constrained in the substantially circular shape. The core element may then be deployed to an expanded state to serve a variety of medical purposes.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

The present invention is directed to medical catheters that may be modularly constructed to facilitate manufacture and/or provide properties that may be difficult to achieve with a catheter formed from a single extrusion. In the context of the present invention, the term "modular" relates generally to a device having more than one component. As described below, the catheter may be constructed of one or more core elements that may be partially or completely surrounded by a jacket member in a variety of configurations.

In the present application, the term "proximal" refers to a direction that is generally towards a physician during a medical procedure, while the term "distal" refers to a direction that is generally towards a target site within a patent's anatomy during a medical procedure.

Figure 1A:
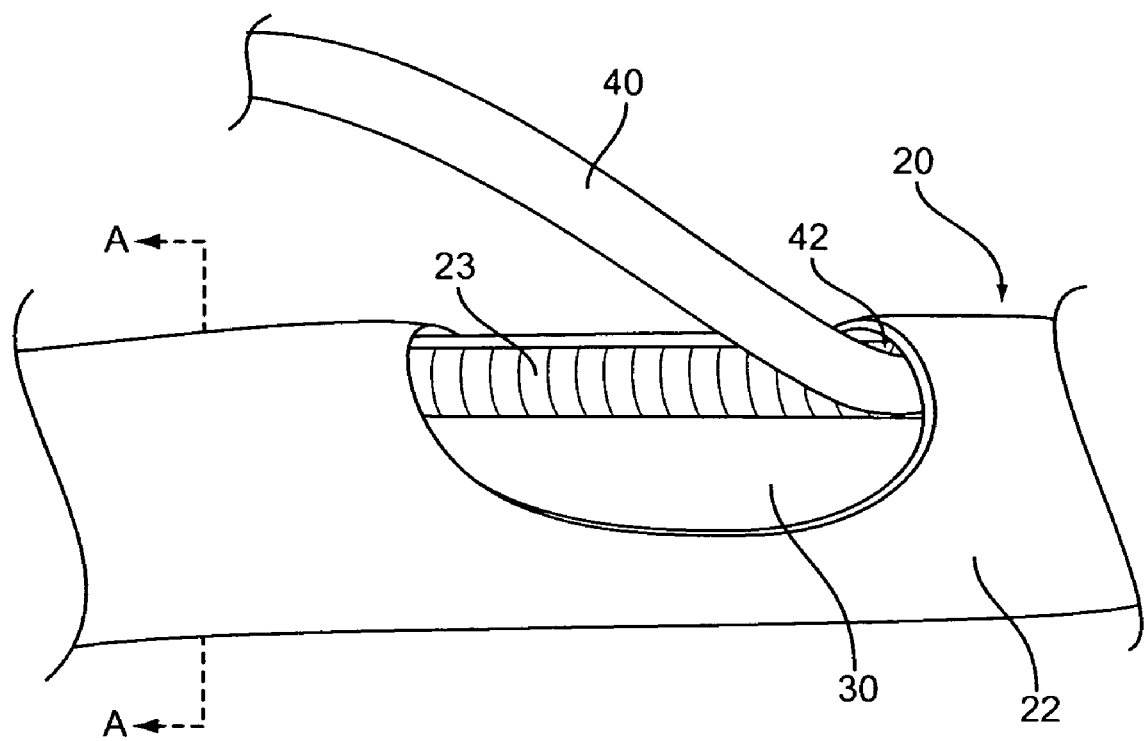
FIGS. 1A-1B are, respectively, a perspective view of a catheter provided in accordance with a first embodiment of the present invention, and a cross-sectional view of the catheter along line A—A.
Figure 1B:
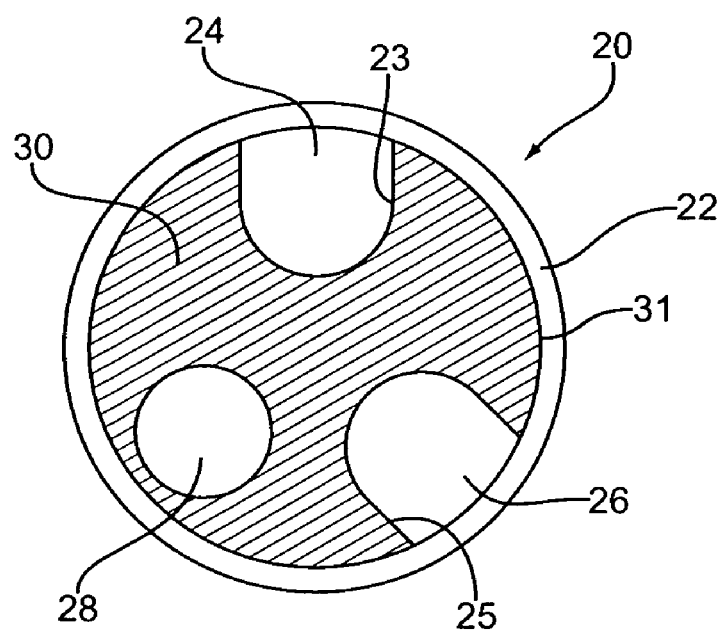

Referring now to FIGS. 1A-1B, a first catheter provided in accordance with principles of the present invention is described. In FIG. 1, catheter 20 comprises core element 30, which has proximal and distal regions and a longitudinal axis. Catheter 20 further comprises jacket member 22, which may be disposed circumferentially around core element 30 along at least a portion of its longitudinal axis.

In the embodiment of FIGS. 1A-1B, core element 30 of catheter 20 comprises a substantially circular main body having an exterior surface 31. As will be described in greater detail below, catheters provided in accordance with the present invention may comprise multiple core elements, each having various configurations. Further, while core element 30 of FIGS. 1A-1B preferably spans an entire longitudinal length of catheter 20, multiple core elements may be provided along the length of a modular catheter in overlapping or abutting fashion, for example, as described with respect to FIGS. 7A-7B hereinbelow.

Referring to FIG. 1B, channels 23 and 25 may be formed in exterior surface 31 of core element 30. The channels may serve a variety of functions. For example, when channels 23 and 25 are covered by jacket member 22, corresponding lumens 24 and 26 are formed in catheter 20, as depicted in FIG. 1B. As will be apparent to one skilled in the art, any number of channels may be provided around the circumference of core element 30. Further, the channels may comprise various configurations, such as U-shaped, semi-circular shaped, rectangular-shaped, and so forth.

Advantageously, the modular construction of catheter 20 permits the formation of side lumens that are substantially close to an exterior surface of catheter 20. Typically, for catheters having a single core extrusion, it may be difficult to form a lumen that is in close proximity to an exterior region of the extrusion. The present invention permits formation of even the smallest lumens adjacent to an exterior surface of catheter 20, based on the size of a channel formed in exterior surface 31 of core element 30. Further, if jacket member 22 is formed of a relatively high strength material, the thickness of jacket member 22 may be reduced, thereby increasing the size of side lumens 24 and 26. Advantageously, a thinner jacket member may permit more lumens to fit within a given cross-section of catheter 20, and/or may reduce the overall cross-section dimensions of catheter 20.

By providing a modular catheter in accordance with principles of the present invention, one or more core elements 30 may comprise different properties than jacket member 22. For example, the component used for core element 30 may comprise a strong yet flexible material, for example, a thermoplastic elastomer such as polyurethane, polyester copolymers or an elastomeric alloy. Alternatively, silicone rubber may be used. Further materials suitable for core element 30 will be apparent to one skilled in the art.

Advantageously, the materials used for jacket member 22 may encompass different properties than the materials used for core element 30. For example, jacket 22 may comprise a biocompatible, lubricious material. One exemplary material is polytetrafluoroethylene (PTFE). Therefore, by employing a modular construct in accordance with the present invention, a relatively strong and flexible core element may be used in conjunction with a lubricious jacket member. Further, an exterior surface of jacket member 22 may be selectively provided with a desired coating, such as a hydrophilic coating, depending on the needs of the surgical procedure.

Further, jacket member 22 may comprise a material having translucent or transparent properties. Such construction may facilitate viewing of objects within catheter 20. For example, a physician may endoscopically view movement of wire guide 40 within side lumen 24 because jacket member 22 is translucent or transparent. This enhanced visualization may not be achievable if catheter 20 had been fabricated of one material, such as an opaque thermoplastic polymer having a wire guide lumen formed therein.

In accordance with another aspect of the present invention, if one or more channels are not fully covered by jacket member 22, then an external access port may be provided. For example, a section of jacket member 22 that was covering channel 23 may be removed to form access port 42, as shown in FIG. 1A.

In one embodiment, access port 42 may be adapted for use in short wire or intraductal exchange procedures. More specifically, wire guide 40 is inserted into a patient's body cavity and guided to a target location. Catheter 20 is then advanced over wire guide 40 via side lumen 24. Wire guide 40 may exit side lumen 24 at access port 42, i.e., in a region where jacket member 22 does not cover channel 23, as shown in FIG. 1A. Using this technique, the length of wire guide 40 may be significantly reduced to facilitate a surgical procedure since only a portion of catheter 20 is coupled to wire guide 40.

Alternatively, a full-length wire guide may be employed in conjunction with catheter 20. The full-length wire guide may be inserted into a patient's body cavity and guided to a target location. The distal end of catheter 20 is then inserted over a proximal end of the wire guide, for example, using side lumen 24 or 26, or alternatively, internal lumen 28. Once the catheter is guided to the target location, a variety of procedures may be performed, such as an imaging procedure and/or an interventional procedure.

In another embodiment, jacket member 22 may be manufactured using a splittable material to allow a wire guide to be removed from one of the channels. While most thin polymer jacket members may be split with sufficient lateral force applied against it, it is preferred that the polymeric materials produce a clean, straight split when the wire guide is removed.

In a still further alternative embodiment, jacket member 22 may comprise one or more perforations (not shown). In one embodiment, the perforations may be formed in a distal region of jacket member 22 that overlays channel 25. Fluid may be infused via side lumen 26 and may exit the catheter at a target location via the perforations disposed in the jacket member.

Modular catheter 20 also may be used in conjunction with an imaging system that is integral to, or separate from, catheter 20. For example, endoscopic visualization may be performed through lumen 28 by employing fiber optic lines coupled to an external viewing device. Alternatively, intravascular ultrasound (IVUS) or other imaging technique may be performed in conjunction with catheter 20.

One or more balloons (not shown) may be provided on an exterior surface of jacket member 22. The balloons may be provided on a distal region of catheter 20, in fluid communication with one or more lumens 24, 26 and 28. Fluid communication may be achieved by forming a side port (not shown) in a lateral surface of jacket member 22, such that the side port is disposed within the confines of the balloon and coupled to a corresponding lumen. The balloon may be selectively inflated for a variety of purposes, e.g., during a balloon angioplasty procedure, dilation and/or stone extraction.

In a still further application, catheter 20 may be used to deploy a self-expanding member, such as a shape-memory stent (not shown). For example, a stent may be provided in a collapsed delivery configuration around an exterior surface of jacket member 22, and an exterior sheath (not shown) may cover jacket member 22 to restrain the stent in the delivery configuration. Once catheter 20 is guided to a target location, the outer sheath may be retracted proximally with respect to jacket member 22 to expose the stent and permit its expansion within a body cavity.

In alternative embodiments of the present invention, multiple jacket members may be employed along a longitudinal and/or circumferential length of catheter 20. The jacket members may have similar or different characteristics, depending on the needs of a procedure. For example, a first jacket member may be disposed over the entire circumference of catheter 20 along its proximal region, while a second jacket member may be disposed over the circumference of a distal region of catheter 20. Alternatively, a first jacket member may be partially disposed about a circumferential region of catheter 20, e.g., covering channel 23, while a second jacket member may be disposed over another circumferential region, e.g., covering channel 25, and so forth.

Figure 2:
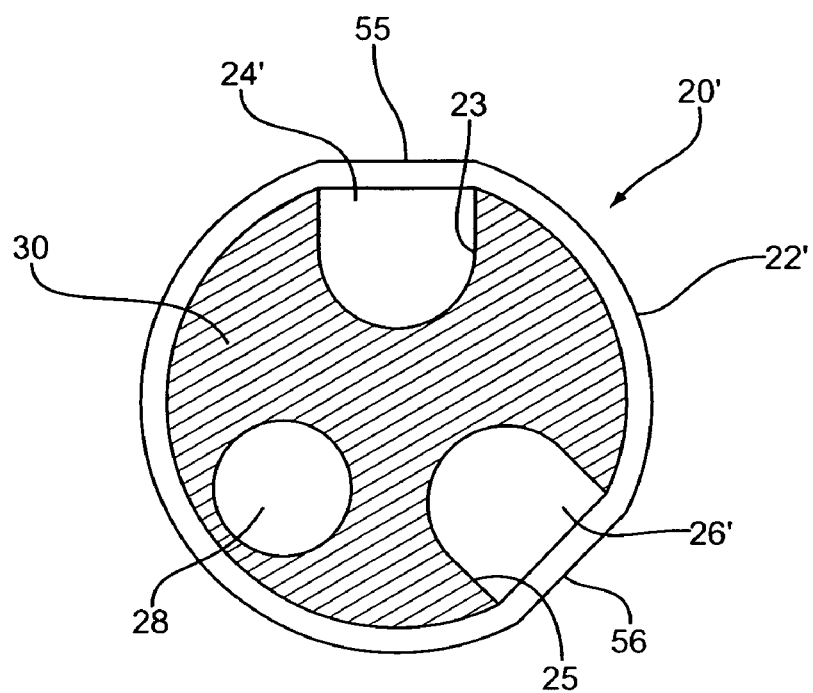
FIG. 2 illustrates a cross-sectional view of a catheter provided in accordance with an alternative embodiment of the present invention.

Referring now to FIG. 2, an alternative embodiment of the present invention is described. In FIG. 2, catheter 20' is similar to catheter 20 of FIGS. 1A-1B, with a main exception that jacket member 22' comprises a shrinkable material. One example of a shrinkable material suitable for use with the present invention is heat-shrinkable polytetrafluoroethylene (PTFE), although other materials may be employed. The shrinking of jacket member 22' in the vicinity of channel 23 forms taut region 55 having side lumen 24' contained therein. Similarly, taut region 56 is formed above channel 25 to contain side lumen 26' therein. By shrinking jacket member 22', an enhanced coupling between the jacket member and core element 30 may be achieved.

Figure 3:
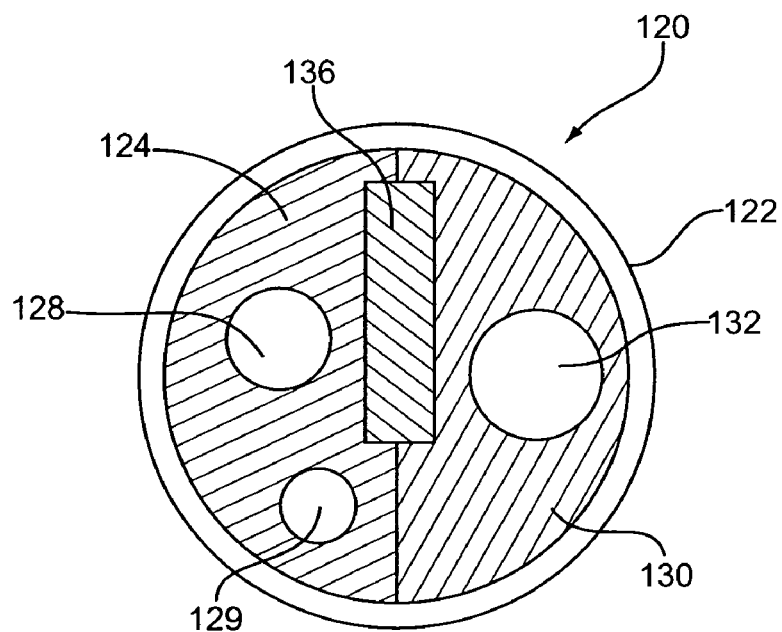
FIG. 3 illustrates a cross-sectional view of a catheter provided in accordance with a further alternative embodiment of the present invention.

Referring now to FIG. 3, a further alternative embodiment of the present invention is described. In FIG. 3, catheter 120 comprises multiple core elements coupled together by at least one jacket member 122. In a preferred embodiment, jacket member 122 comprises a shrinkable material, such as heat-shrinkable PTFE, that permits the core elements to be held together to form the overall catheter structure.

In the embodiment of FIG. 3, three core elements are provided. Catheter 120 comprises first core element 124 having lumens 128 and 129 formed therein, second core element 130 having lumen 132 formed therein, and third core element 136. While the core elements of FIG. 3 show two substantially semi-circular core elements having a rectangular core element disposed therebetween, any number of core element configurations may be provided. For example, the core elements may be square-shaped, circular, oval-shaped, pie-shaped, and so forth.

Further, as will be apparent to one skilled in the art, catheter 120 may comprise fewer or greater than three core elements, and each core element may have one or more lumens, or no lumen whatsoever, as generally depicted in FIG. 3. Further, catheter 120 may comprise side lumens formed from channels, as described with respect to FIGS. 1-2 above. If lumens are provided within the core elements, they may be used for any number of purposes ranging from serving as a wire guide lumen, fluid aspiration or infusion conduit, device delivery lumen, imaging channel, and so forth.

Figure 4A:
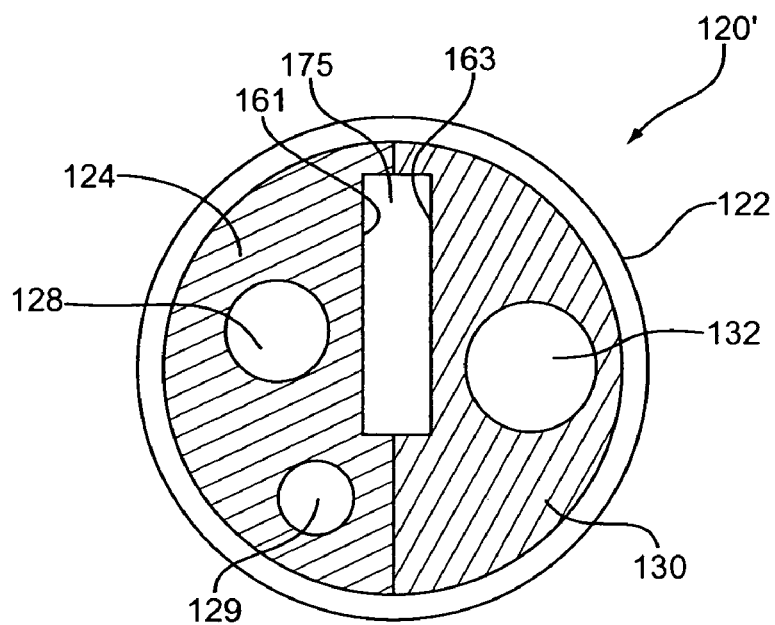
FIGS. 4A-4B illustrate cross-sectional views of catheters provided in accordance with further alternative embodiments of the present invention.

Additionally, void spaces may be formed between core elements. For example, catheter 120' of FIG. 4A is similar to catheter 120 of FIG. 3, with the exception that third core element 136 has been removed. As shown in FIG. 4A, void region 175 is formed in a central region of catheter 120'. The void region may be formed by providing indentation 161 on semi-circular first core element 124, and further providing opposing indentation 163 on semi-circular second core element 130. Alternatively, void region 175 may be formed by providing an indentation within only one of the core elements. Void region 175 may be used as a conduit to deliver fluids, instruments, and perform other functions.

As will be apparent to one skilled in the art, the void region may be provided along any region about the cross-section of catheter 120', for example, it may be formed in a central region as shown in FIG. 4A, or alternatively, near an exterior region such that jacket member 122 fully or partially encloses the void region. If desired, void region 175 may span the entire longitudinal length of catheter 120', or may only span a portion of its length.

Figure 4B:
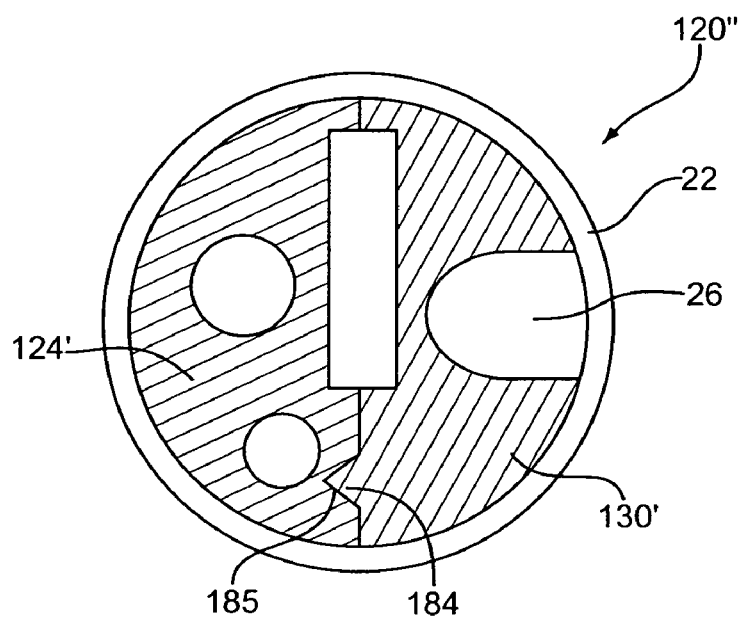

In addition, the core elements may securely interlock, as generally depicted in FIG. 4B. Specifically, the elements of catheter 120" are similar to the elements of catheter 120', with the main exception that first core element 124' comprises indentation 185 disposed therein, and second core element 130' comprises protrusion 184, which is configured to securely interlock with indentation 185. While nested triangular protrusions and indentations are depicted in FIG. 4B, any number of interlocking shapes may be provided. It should also be noted that any of the embodiments described above may employ the interlocking components of FIG. 4B, and may further employ any combination of side lumens, void regions and other components depicted herein.

The modular catheter embodiments shown in FIGS. 3-4 have several advantages over previously-known catheters that are manufactured by a single extrusion, or formed by co-extrusion of two or more materials into a single profile. In particular, the latter method is relatively complex, and may not be feasible when the processing temperatures of different materials are disparate. However, in the present invention, core elements 124 and 130, and optionally core element 136, may be held together, even if they have different material properties. For example, third core element 136 may comprise a substantially rigid metal strip having a compliance that is different than core elements 124 and/or 130.

Additionally, the core elements of FIGS. 3-4, which need not be thermally fused together, may be movable relative to one another. For example, third core element 136 of FIG. 3 may be slidable longitudinally with respect to first and second core elements 124 and 130, respectively. Such movement may occur when the catheter is inserted through tortuous vasculature, i.e., the design permits the core elements to move with respect to one another to help the catheter conform to the anatomy. Alternatively, movement of the core elements may occur by manual manipulation by a physician, e.g., by proximally retracting or distally advancing proximal ends of the individual core elements, or mechanisms operably coupled to thereto. By permitting core elements to slide with respect to one another, catheter 120 may change its fundamental shape and/or physical properties. Further, distal advancement of one or more core elements 124, 130 and 136 beyond the distal end of catheter 120 may have functional purposes, either in combination with, or in lieu of, advancing other instruments through their associated working lumens.

Figure 5A:
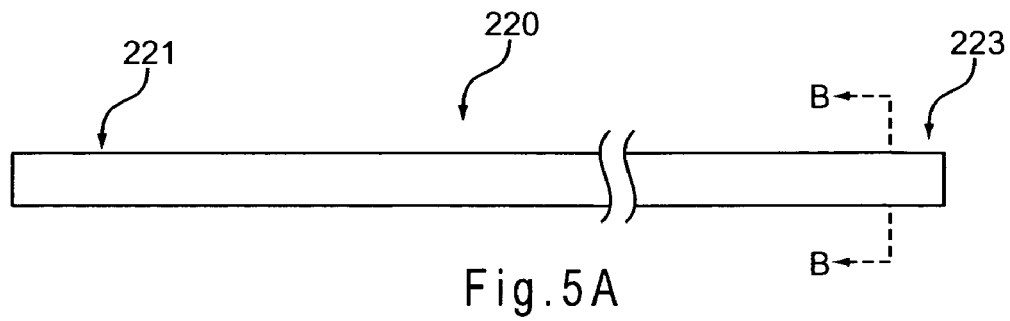
FIGS. 5A-5E illustrate, respectively, a side view of a catheter provided in accordance with an alternative embodiment of the present invention, cross-sectional views of the catheter of FIG. 5A along line B—B in constrained and unconstrained states, a side-sectional view of an alternative embodiment of the catheter of FIGS. 5A-5C, and a cross-sectional view of a further alternative embodiment of FIGS. 5A-5C.
Figure 5B:
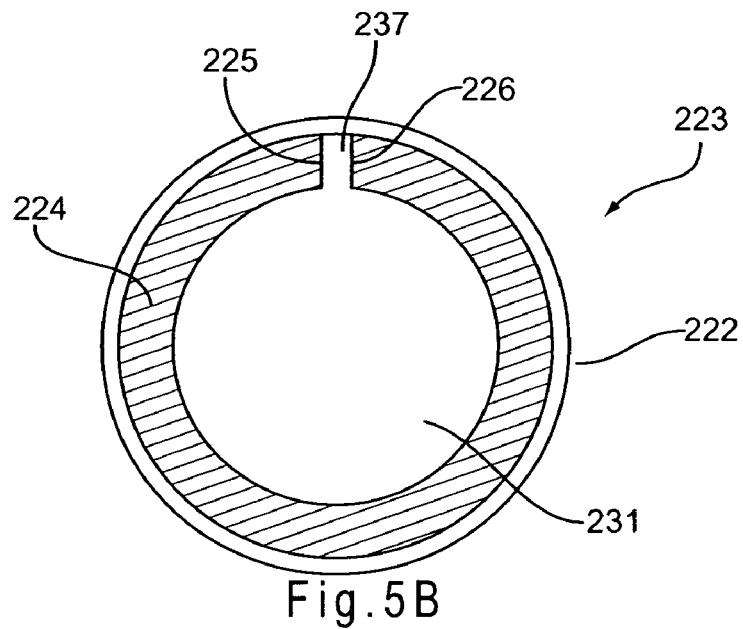
Figure 5C:
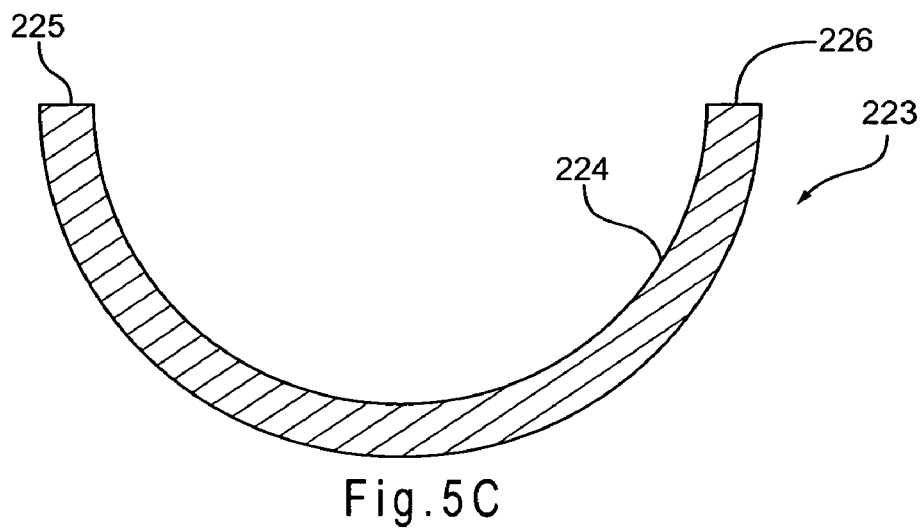

Referring now to FIGS. 5A-5C, a further alternative embodiment of a modular catheter provided in accordance with the present invention is described. Catheter 220 has proximal region 221 and distal region 223, as shown in FIG. 5A. The catheter comprises at least one core element 224 having first end 225 and second end 226, and further comprises jacket member 222, as shown in FIG. 5B. Core element 224 preferably is flexible and may move from a constrained state, depicted in FIG. 5B, to a relaxed, expanded state, as shown in FIG. 5C.

In a preferred embodiment, core element 224 is provided along at least a portion of distal region 223, and more preferably, at the distal most end of catheter 220. In this case, another core element (not shown) may be disposed within jacket member 222 at a location proximal to core element 224. Preferably, a non-expandable circular core element having a lumen therein (not shown) is disposed proximal to, and abutting, core element 224.

In use, core element 224 is held in the constrained configuration by jacket member 222, as shown in FIG. 5B. Jacket member 222 may shrink about the constrained core element, e.g., by employing heat-shrink tubing. Core element 224 is held in the constrained state by jacket member 222 such that first and second ends 225 and 226 form a substantially circular shape that conforms to an interior surface of jacket member 222. In the constrained state, it is preferred that first end 225 does not touch second end 226, thereby forming gap 237 therebetween. Further, when core element 224 is constrained in a substantially circular configuration, lumen 231 may be formed therein, as shown in FIG. 5B.

Catheter 220 may be delivered into a patient's body cavity with core element 224 being in the constrained state. Lumen 231 may be employed as a wire guide lumen to guide catheter 220 to a target location. Additionally, infusion or aspiration may be provided through lumen 231, or medical instruments may be delivered therethrough. If a circular core element having a lumen therein is disposed proximal to core element 230, as discussed above, its lumen preferably is in fluid communication with lumen 231.

When catheter 220 is positioned at a desired location, core element 224 may be deployed by proximally retracting jacket member 222 with respect to core element 224. When core element 224 is no longer constrained by jacket 222, it may return to its relaxed, expanded state, as shown in FIG. 5C. In the expanded state, core element 224 may be used to apply a radially outward pressure within a body cavity. If used in a vessel, core element 224 may function like a stent by being configured to expand the vessel in a radially outward direction.

In an alternative embodiment, core element 224 may be transferred from the constrained state to the expanded state by employing a cutting instrument (not shown). The cutting instrument may be delivered through lumen 231, and may selectively cut through jacket member 222 via gap 237. Once the jacket member has been cut, it no longer constrains core element 224 and permits its expansion within a body cavity.

Figure 5D:
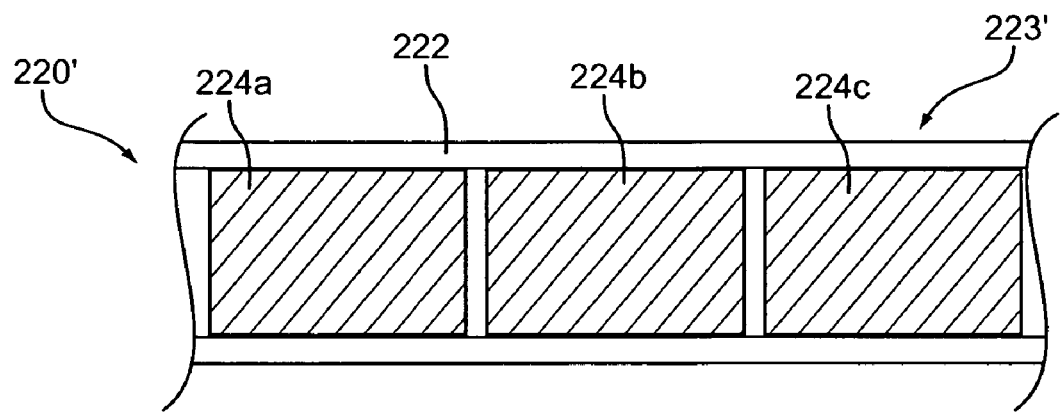

Referring now to FIG. 5D, an alternative embodiment of catheter 220 is provided. Distal end 223' of catheter 220' houses multiple core elements 224a, 224b and 224c. As will be apparent to one skilled in the art, greater or fewer than three core elements may be provided, and they may be similar to core element 224 of FIGS. 5B-5C. In the embodiment of FIG. 5D, proximal retraction of jacket member 222 with respect to the constrained core elements will first deploy core element 224c. Further proximal retraction of the jacket member may deploy core elements 224b and 224a, respectively, at desired target sites.

Figure 5E:
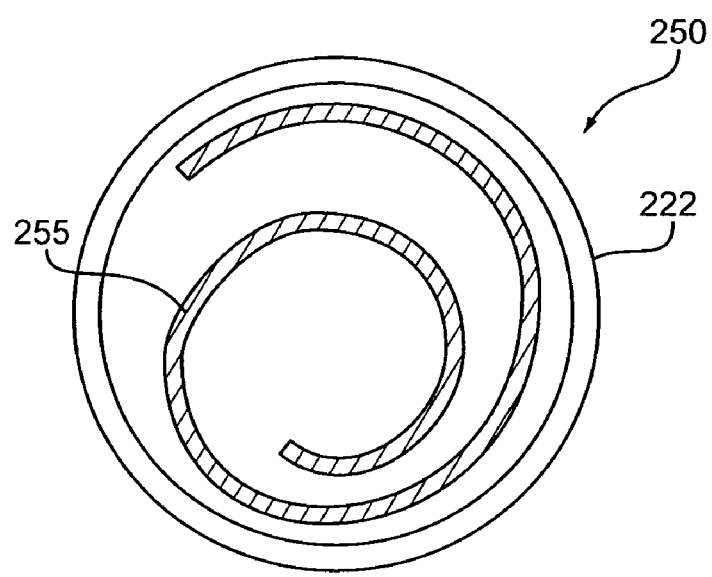

It will be apparent to one skilled in the art that while a generally semi-circular shaped core element has been shown constrained in a generally circular position, any number of constrained and unconstrained core element shapes may be employed. For example, in the embodiment of FIG. 5E, core element 255 of catheter 250 comprises a coil-shape in the constrained configuration when housed within jacket member 222, and may expand to a larger coil-shape or a circular shape when deployed.

Still further expandable core element shapes may be employed. For example, in the embodiment of FIG. 3, third core element 136 may be retained in a constrained state when disposed between first and second core elements 124 and 130, and further held in place by jacket member 122. However, if third core element 136 is advanced distally beyond catheter 120, such that it is no longer constrained by jacket member 122, it may assume an expanded shape. In such embodiments, a core element may return to a predetermined, expanded configuration due to its mechanical properties, or because the core element comprises a shape-memory material such as Nitinol.

Figure 6A:
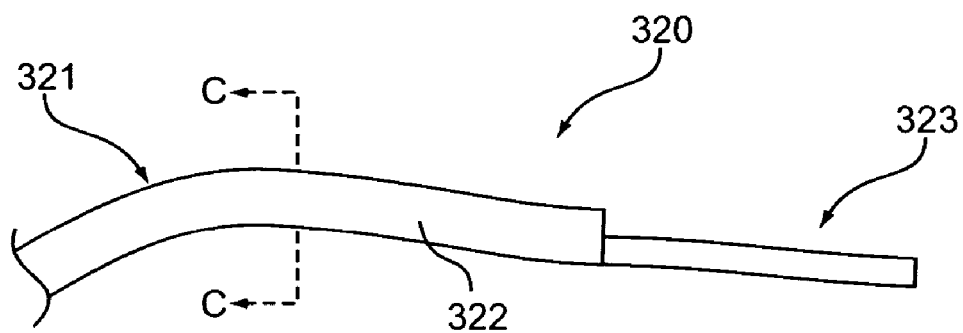
FIGS. 6A-6B are, respectively, a side view of a catheter provided in accordance with an alternative embodiment of the present invention, and a cross-sectional view of the catheter of FIG. 6A along line C—C.
Figure 6B:
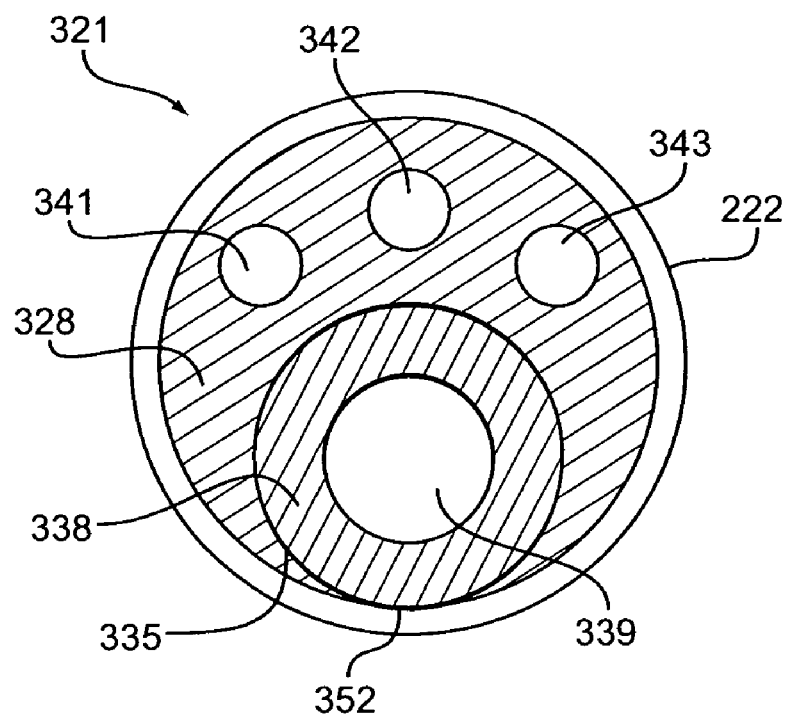

Referring now to FIGS. 6A-6B, a further alternative embodiment of the present invention is described. In FIG. 6A, catheter 320 comprises proximal region 321 and distal region 323. As shown in FIG. 6B, proximal region 321 comprises first core element 328 and second core element 338. Second core element 338 may be disposed substantially coaxially within a portion of first core element 328. In this embodiment, first core element 328 may comprise longitudinal bore 335, and second core element 338 may be adapted to be seated within bore 335. Second core element 338 may be partially directly exposed to jacket member 322 at region 352, as shown in FIG. 6B.

In the embodiment of FIGS. 6A-6B, distal region 323 may only comprise second core element 338. Advantageously, by providing a modular catheter in accordance with catheter 320, it is possible to provide a catheter having a variable cross-section along its longitudinal axis. In particular, it may be desirable to construct the catheter having a smaller outer diameter along distal region 323, and a relatively larger diameter along proximal region 322, as generally depicted in FIG. 6A. Alternatively, first core element 328 may extend distal to second core element 338, i.e., in a manner that is opposite to the distal region 323 depicted in FIG. 6A.

First core element 328 may comprise one or more lumens, e.g., auxiliary lumens 341, 342 and 343, while second core element 338 may comprise working lumen 339. During a medical procedure, catheter 320 may be advanced over a wire guide via one of the lumens. Further, any of the lumens may be used to provide for fluid aspiration, infusion, or the delivery of surgical devices. In one embodiment, working lumen 339 may provide for the delivery of devices to a target site, while auxiliary ports 341, 342 and 343 may provide for the delivery of devices, infusion or aspiration at a location proximal to the target site.

Alternatively, first core element 328 and jacket member 322 may initially span the entire length of catheter 320, i.e., they may extend along distal region 323 such that the outer diameter along the length of catheter 320 is substantially uniform. At any time during a procedure, a physician may proximally retract first core element 328 and jacket member 322 with respect to second core element 338, for example, to obtain the configuration depicted in FIG. 6A. The retraction may be achieved by pulling proximal ends of first core element 328 and jacket member 322, or any mechanisms that are operably coupled thereto. At this time, the entire catheter assembly may be further maneuvered as one unit, e.g., by advancing the assembly of FIG. 6A distally within a vessel. Alternatively, a physician may further retract first core element 328 and jacket member 332, or may retract the entire assembly.

Figure 7A:
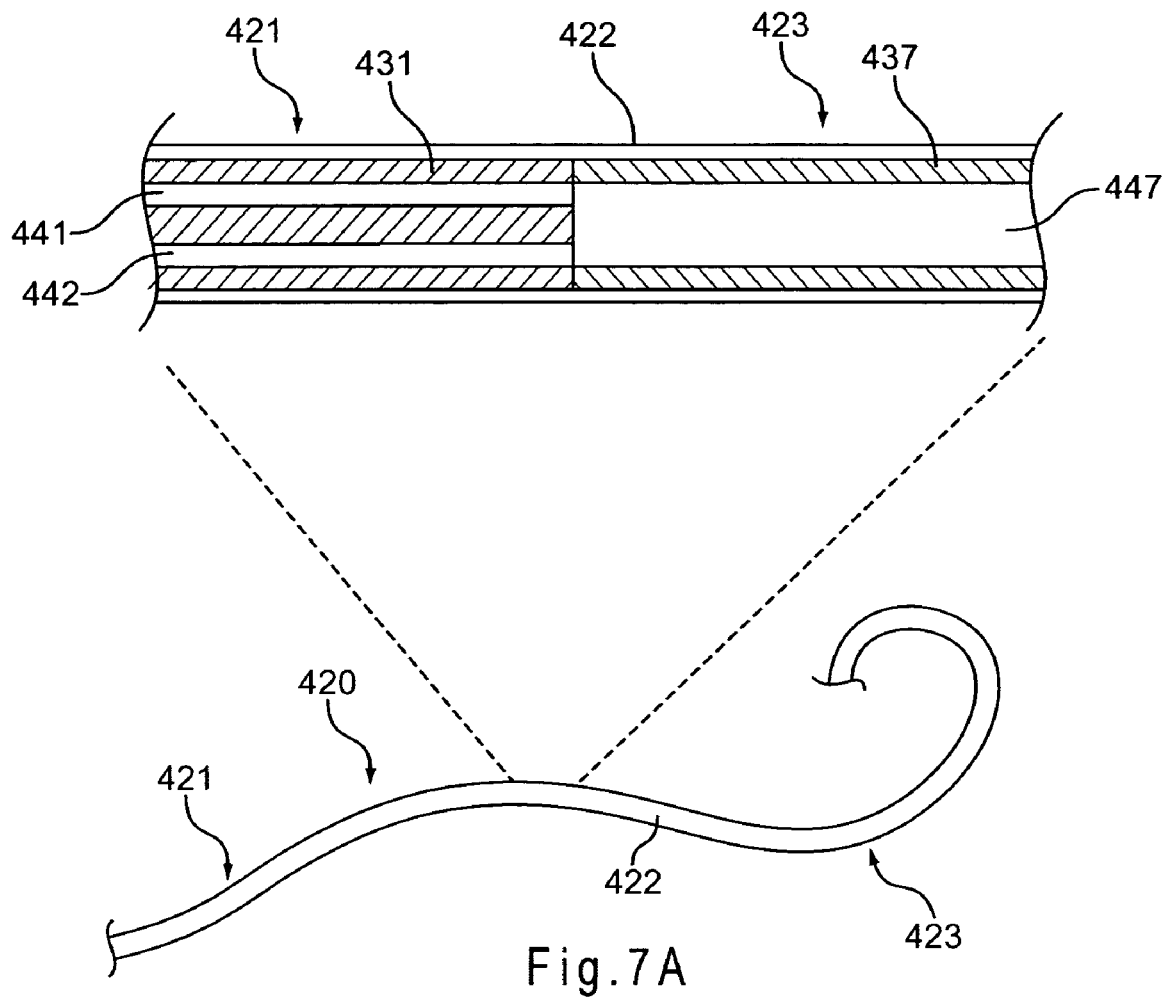
FIGS. 7A-7B illustrates, respectively, a side sectional view and side view of a catheter provided in accordance with a further alternative embodiment of the present invention, and a side sectional view of an alternative embodiment of the catheter of FIG. 7A.
Figure 7B:
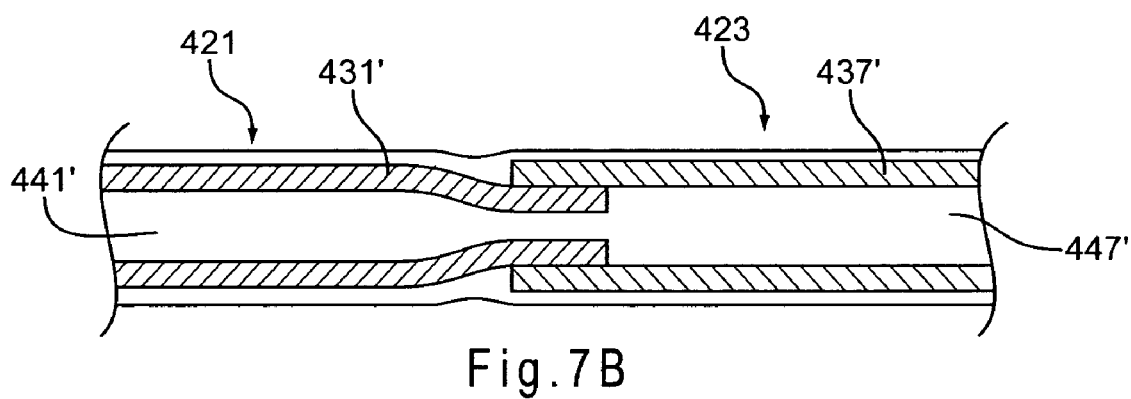

Referring now to FIGS. 7A-7B, further alternative embodiments of the present invention are described. In FIG. 7A, catheter 420 comprises proximal region 421 and distal region 423. Proximal region 421 comprises first core element 431, while distal region 423 comprises second core element 437. In a preferred embodiment, one jacket member 422 is disposed along the entire length of catheter 420, such that the jacket member circumferentially surrounds first core element 431 and second core element 437. First core element 431 may comprise a distal end that abuts a proximal end of second core element 437, as depicted in FIG. 7A, or alternatively, first core element 431' may partially overlap with second core element 437', as shown in FIG. 7B. In the embodiment of FIG. 7B, a distal portion of first core element 431' tapers into second core element 437', thereby permitting fluid communication between lumens 441' and 447'.

By providing proximal and distal regions comprising different core elements, catheter 420 may have variable properties along its longitudinal axis. For example, proximal region 421 may comprise a core element having elastomeric properties, while distal region 423 may comprise a core element having malleable properties, as schematically shown in the full-length side view of FIG. 7A. As will be apparent to one skilled in the art, either core element may comprise substantially rigid properties. For example, during a coronary intervention, it may be desirable to provide proximal region 421 with a relatively rigid core element, while distal region 423 comprises a relatively flexible or malleable core element.

Further, either of core elements 431 or 437 may comprise one or more lumens formed therein. As shown in FIG. 7A, first core element 431 comprises first lumen 441 and second lumen 442, while second core element 437 comprises lumen 447. Therefore, fluid communication may be provided from lumens 441 and 442 into lumen 447.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

I claim:

1. A catheter comprising:
    a first core element having proximal and distal regions and a longitudinal axis;
    a second core element having proximal and distal regions and a longitudinal axis; and
    a jacket member disposed at least partially around the first core element and the second core element,
    wherein at least the one of the first core element and second core element comprises an indentation formed in a surface thereof, the indentation forming a void region between the first core element and second core element that is suitable for use as a catheter lumen.

2. The catheter of claim 1 wherein the first core element is longitudinally movable with respect to the second core element.

3. The catheter of claim 1 wherein the first core element at least partially surrounds the second core element.

4. The catheter of claim 1 wherein the second core element extends distal to the first core element.

5. The catheter of claim 4 wherein the catheter comprises a distal region of reduced cross-section relative to a proximal region of the catheter.

6. A method of manufacturing a catheter, the method comprising:
    providing a first core element comprising an elongated body having a longitudinal axis and proximal and distal regions;
    providing a second core element comprising an elongated body having a longitudinal axis and proximal and distal regions;
    at least partially surrounding the first core element and second core element using a jacket member; and
    forming a lumen in a void region between the first core element and the second core element, wherein the void region is formed from at least one indentation made in a lateral surface of at least the first core element or second core element.

7. The method of claim 6 wherein the first core element is longitudinally movable with respect to the second core element to vary a shape of the catheter.

8. The method of claim 6 further comprising at least partially surrounding the second core element with the first core element.

9. The method of claim 8 further comprising extending the second core element distal to the first core element, thereby allowing the catheter to comprise a distal region of reduced cross-section relative to a proximal region of the catheter.

10. A catheter comprising:
a first core element having proximal and distal regions and a longitudinal axis;
a second core element having proximal and distal regions and a longitudinal axis; and
a jacket member disposed at least partially around the first core element and the second core element,
wherein the first core element and the second core element lack a fixed attachment to one another along their respective longitudinal axes.

11. The catheter of claim 10 wherein a distal end of the first core element is selectively longitudinally movable beyond a distal end of the second core element.

12. The catheter of claim 10 wherein the first core element is formed from a material, and there is a lumen formed within the material of the first core element.

13. The catheter of claim 10 wherein the first core element at least partially surrounds the second core element.

\* \* \* \* \*